United States Patent [19]

Heath

[11] 4,014,382
[45] Mar. 29, 1977

[54] TEMPERATURE AND/OR RELATIVE HUMIDITY CONTROL SYSTEM

[75] Inventor: Walter I. Heath, Monnford, Okla.

[73] Assignee: Basil E. Demeur, Chicago, Ill.

[22] Filed: May 21, 1975

[21] Appl. No.: 579,322

[52] U.S. Cl. .................................. 165/60; 128/186; 128/192; 261/DIG. 65
[51] Int. Cl.² .......................................... F24F 3/14
[58] Field of Search ............... 165/60; 261/55, 153, 261/156, DIG. 65; 128/186, 187, 192, 193, 194, 212

[56] References Cited

UNITED STATES PATENTS

| 2,116,328 | 5/1938 | Silten | 128/192 |
|---|---|---|---|
| 2,774,346 | 12/1956 | Halliburton | 128/186 |
| 3,415,313 | 12/1968 | Olstad | 165/60 |
| 3,420,232 | 1/1969 | Bickford | 261/DIG. 65 |
| 3,534,732 | 10/1970 | Bickford | 261/DIG. 65 |
| 3,565,072 | 2/1971 | Gauthier | 128/212 |
| 3,756,577 | 9/1973 | Breiling | 261/DIG. 65 X |
| 3,864,440 | 2/1975 | Giocoechea | 261/DIG. 65 |

Primary Examiner—C. J. Husar
Assistant Examiner—Daniel J. O'Connor
Attorney, Agent, or Firm—Dominik, Knechtel, Godula & Demeur

[57] ABSTRACT

A device for independently controlling the temperature and/or relative humidity in the gas utilized in connection with a life support system formed by a chamber bounded by a bottom wall, side walls, and a top wall, one of the walls of the chamber provided with a gas inlet and a gas outlet, gas spider means associated with the gas inlet and providing gas passageways for segregating portions of the gas introduced into the device through the gas inlet, gas proportioning valve means positioned in association with the gas spider means and in line with the gas inlet to permit independent variable proportioning of the gases to at least two downline gas passageways, at least a first gas passageway traversing the gas spider means and terminating at the gas outlet and a second gas passageway traversing the gas spider means and in fluid communication with the chamber, the gas outlet being in fluid communication with the chamber and with the first passageway in the gas spider means, the chamber being adapted to hold a quantity of a fluid for humidifying the gas traversing therethrough, such that gas introduced into the system through the gas inlet may be variably proportioned to direct a portion of the gas through the gas spider means to the gas outlet, that gas being dry in nature, and another portion of the gas directed to a second passageway for introduction into the chamber to humidify the same and exiting the humidified gas into a passageway to admix with the first gas portion thereby forming a gas mixture having a controlled relative humidity. It is further contemplated to incorporate heat means such that gases may similarly be heated as well as humidified to achieve a gas admixture readily adjustable with respect to temperature and relative humidity.

19 Claims, 6 Drawing Figures

TEMPERATURE AND/OR RELATIVE HUMIDITY CONTROL SYSTEM

BACKGROUND OF THE INVENTION

It is generally known and acknowledged that patients involved in respiratory therapy require the inhalation of life-supporting gases, generally including oxygen and/or air. It is further known that it is far more beneficial for the patient to receive such gases under conditions of heat and humidity rather than to supply the patient with merely a dry cool gas. It has been found, for example, that when the inhaled gas is both heated and humidified, the patient is more receptive to the gas especially in connection with minimizing other potential respiratory diseases when involved in respiratory therapy. The present invention is a device which seeks to improve upon known systems for providing both heated and humidified gases to a patient involved in respiratory therapy, or involved in other systems wherein there is a requirement for the provision of life-support gases to be inhaled.

To date, no device has been developed which permits the operator thereof to readily adjust the system to provide inhaled gas at a given temperature and relative humidity. Devices of this type to accomplish humidification have generally been nothing more than humidification boxes through which a gas is bubbled via a gas inlet directing the gas into the humidification chamber, bubbling the same through heated water and the heated humidified gas being captures in a gas outlet and directed to the patient. It will be appreciated that in order to vary the temperature and/or humidity level of the gases, a great deal of manipulation is necessary as well as time, since it is not possible to, readily, change the temperature of the exiting gas without first changing the temperature of the water through which the gas is bubbled. For example, such devices generally require that the operator change the temperature of the heater in order to further heat the water in the chamber which accomplishes both higher heat level for the gas as well as a higher humidification level. It will, therefore, be appreciated that it has not been possible to independently control both temperature and humidity with such devices.

Another problem associated with such systems is that once the heated and humidified gas exits the humidifier and travels the path to the patient's support system such as a face mask or the like, the gas has a tendency to cool which causes a condensation of water in the patient's gas delivery tube.

Exemplary of the types of devices presently employed in solving the problem of heating and humidifying the gases to be inhaled is shown in U.S. Pat. No. 3,659,604. It will be observed that the device disclosed and claimed therein involves the provision of a heating chamber wherein water is contained, the water being heated by a heater and gas being introduced into the chamber, picking up moisture from the humidification element, and exiting the system through a gas outlet for passage on to the patient. In order to prevent the gas from losing temperature as it traverses the hose connected to the patient, a heating element is provided in longitudinal arrangement in the exit hose such that gases are heated for a distance as they pass to the patient. It will be appreciated that even with this system, efficient and rapid variation of the temperature and/or humidity is difficult, if not impossible since it still involves the requirement of changing the temperature of the water within the chamber in order to affect the commitant change in the temperature of the gas. Furthermore, the subject device does not actually control the relative humidity of the gas, but only the humidification level of the gas which passes through the system.

Other types of systems available basically fall into two categories, these including the cascade type system which is used mostly on ventilators and the bubble type system which is generally used with a compressed oxygen/air system. Both of these systems operate only when gas under pressure is delivered to the system either from a ventilator or from an oxygen/air source where the gas is under a pressure of at least 50 psi. Heated nebulizers have the advantage of clinically allowing oxygen/air gas mixing from a single compressed oxygen source, however, these units can and do introduce contamination from the water reservoir to the patient via the water particles generated. In generally all of these systems, the temperature of the gas is controlled by controlling the temperature of the water reservoir with an adjustable thermostat. As indicated previously, this method is slow in reaction time and also creates a possible safety hazard by exposing an adjustable thermostat to a wet, oxygen-enriched environment.

The proposed system of the present invention combines the advantage of existing systems but includes unique and new design and functional concepts. In short, the unit of the present invention allows the operator to have an effective fast safe control over several parameters of the system and the gases which flow therethrough. The present system offers a strict water vapor generation with controlled oxygen/air mixing from a single compressed oxygen source. In addition, the temperature control eliminates any exposed adjustable thermostat, but does allow the operator to adjust to any delivered gas temperature from 85° to 114° F. in less than ninety seconds. In addition, the heat control system of the present invention operates at low heating element temperatures thereby allowing the heater to operate safely with no gas flow through the humidifier. Hence, preheating of the humidifier is possible without any danger or other hazards existing. Finally, as to the heating element, it will be noted from the description following below that the heating element is located externally to the sterile humidifier such that the heater need not be sterilized for subsequent use.

The present system also allows the operator to control the relative humidity of the delivered gas. By using the fast reacting temperature and relative humidity controls, the delivery gas can be regulated to meet most clinical situations. For example delivery gas could be regulated to 108° F. at 80% relative humidity when this gas flows through the delivery tubing it would be cooled. As the gas cools, the relative humidity would increase and the gas at the patient end of the delivery tubing would be at 98° F. and 99+% relative humidity. A further advantage is the fact that no condensation occurs in the delivery tube.

OBJECTS AND ADVANTAGES

It will therefore be appreciated that the principal object of the invention is to provide a system for independently controlling the temperature and relative humidity of a gas utilized in connection with a life-support systems especially involved in respiratory therapy, or other life-support systems, wherein the device utilized to heat and humidify the gas essentially segregates the incoming gas into various portions, one portion of the gas traversing the system and remaining in a cool dry condition, another portion of the gas traversing the system and exiting in a hot dry condition, and a third portion of the gas traversing the system and exiting in a hot wet condition, the admixture of these three gases producing a resulting gas for delivery to the patient which controls both temperature and relative humidity.

In connection with the foregoing object, it is yet another object of this invention to provide a system of the type described wherein gas proportioning valve means are provided such that the operator may easily, efficiently and rapidly vary both the temperature and relative humidity of the exiting gases, without at the same time requiring the operatory to vary the temperature of the water in the humidifer, merely by adjusting the proportion of gas blowing through the system to exit in either a cool, dry condition, hot, wet condition, or hot dry condition. It will, therefore, be appreciated that pursuant to this object and advantage, control over the parameters of the exiting gas is achieved by controlling the input and outflow of the gases rather than in controlling the temperature of the heater associated with the unit, or the temperature of the water within the chamber.

Another object of the invention as described herein is to provide a device for controlling the temperature and relative humidity of gases introduced into the device which is formed by a chamber bounded by a bottom wall, peripheral side walls, and a top wall, and adapted to receive and hold a quantity of fluid for humidifying a gas, one of the walls of the chamber provided with a gas inlet and a gas outlet, gas spider means associated with the gas inlet and providing gas passageways for segregating portions of the gas provided to the system through the gas inlet, gas proportioning valve means positioned in association with the gas spider means and in line with the gas inlet thereby to permit the independent variable portioning of gas to at least two downline gas passageways, at least a first passageway traversing the gas spider means and terminating at the gas outlet, and at least a second gas passageway traversing the gas spider means and in fluid communication with the chamber, the gas outlet being in fluid communication with the chamber and with the first passageway in the gas spider means, whereby gas introduced into the system through the gas inlet may be variably adjusted to direct a portion thereof through the gas spider means to the gas outlet, and another portion of the gas directed to a second passageway for introduction into the chamber to humidify the same and exiting the humidifying gas into another passageway to mix with the first gas portion thereby forming a gas mixture having a controlled relative humidity.

In connection with the foregoing object, it is a further object of this invention to provide a system of the type described which further includes heat means associated with the chamber for providing heat to the internal portion of the chamber thereby to heat the water or other fluid contained within the chamber such that gas directed into and through the chamber constitutes a warm wet gas when exiting from the chamber.

Still in connection with the foregoing objects, it is another object of this invention to provide a system and device of the type described wherein the chamber containing the fluid for humidifying the gases is further provided with a heat dispersion means to accomplish the dispersion of the heat throughout the internal portions of the chamber such that the heat is uniformly distributed throughout the fluid contained in the chamber.

A further object of the invention is to provide a device and system of the type described wherein the heat means constitutes a heater associated with the bottom wall of the chamber and located externally thereto such that the heat is provided to the fluid in the chamber from an external source which is removably secured to the system thereby to eliminate the need to sterilize the heater when sterilizing the system for use in connection with respiratory therapy.

Still another object of this invention in connection with the foregoing objects is to provide a device and system of the type described wherein the gas spider means is further provided with additional gas passageways associated with a heat exchanger unit which extends downwardly from the top wall thereby to be positioned within the confines of the chamber and immersed in the fluid or water within the chamber such that gas traversing the gas spider means through the said passageways and traversing the heat exchanger will remain in a dry condition but nevertheless pick up heat from the internal portion of the chamber such that of the gases introduced into the gas inlet, a portion of the gas will traverse the system as cool, dry gas, that being the gas traversing from the gas inlet to the gas outlet, a portion of the gas will traverse the system through the heat exchanger or picking up only heat and no moisture, that portion of the gas exiting into a mixing chamber with the cool, dry gas in the form of hot, dry gas, and a third portion of the incoming gas is directed through the gas spider means into the internal portion of the chamber thereby to become heated and wetted or humidified, and that gas exiting the system into a passageway for admixture with the other gases and exiting in the form of a hot, wet gas, such that in the mixing passageway, the three gases which admix are cool dry gas, hot dry gas, and hot wet gas.

In connection with the foregoing objects, it is yet a further object of this invention to provide a device and system of the type described wherein the gas valve proportion means each consists of a 90° angle wedge element interposed in the corresponding passageway of such that upon the rotational manipulation of the element, the amount of gas permitted to traverse the element is controlled by the operator such that the proportion of gas traversing the system as either cool dry gas, hot dry gas, or hot wet gas, can be accurately and efficiently controlled.

In connection with the foregoing object, it is yet another object of the invention to provide two such 90° angle wedge-shaped elements as gas valve proportioning means, one of said valves located adjacent the gas inlet thereby to proportion gas and control the portion of the gas traversing the gas spider means from the gas inlet to the gas outlet and letting a second portion of the gas traverse said gas spider means to another passageway wherein a second 90° angle wedge-shaped gas valve is positioned thereby to control the portion of the gas to be directed to the heat exchanger versus the portion of gas to be directed into the chamber such that between the two gas valve proportioning means located in the device, the operator can readily control the percentage of the three gases to be admixed for downline introduction to the patient, thereby to control both temperature and relative humidity of the resulting gas mixture.

Further features of the invention pertain to the particular arrangement of the elements and parts whereby the above-outlined and additional operating features thereof are attained.

The invention, both as to its organization and method of operation, together with further objects and advantages thereof, will best be understood by reference to the following specification, taken in connection with the accompanying drawings in which:

BRIEF SUMMARY OF INVENTION

The present invention provides a temperature and relative humidity control system for gases particularly suited for respiratory therapy. The invention is formed by a humidification chamber bounded by peripheral side walls, a bottom wall, and a top wall, the top wall provided with a main gas inlet and a main gas outlet, gas spider means associated with the gas inlet and a heat exchanger means associated with the gas inlet and a heat exchanger means associated with the gas spider means, at least a pair of gas proportioning valves positioned within said gas spider means thereby to proportion the incoming gas into one portion which traverses the gas spider means as a cool dry gas, another portion which traverses the gas spider means and enters the heat exchanger means and exits therefrom in a hot dry condition, and a third portion of gas which traverses the gas spider means and is directed into the humidification chamber to assimilate moisture and become humidified, the three portions of gas then being admixed in a passageway immediately beneath the main gas outlet such that the exiting gas may be quickly and efficiently controlled with respect to both temperature and relative humidity.

DETAILED DESCRIPTION OF INVENTION

Figure 1:
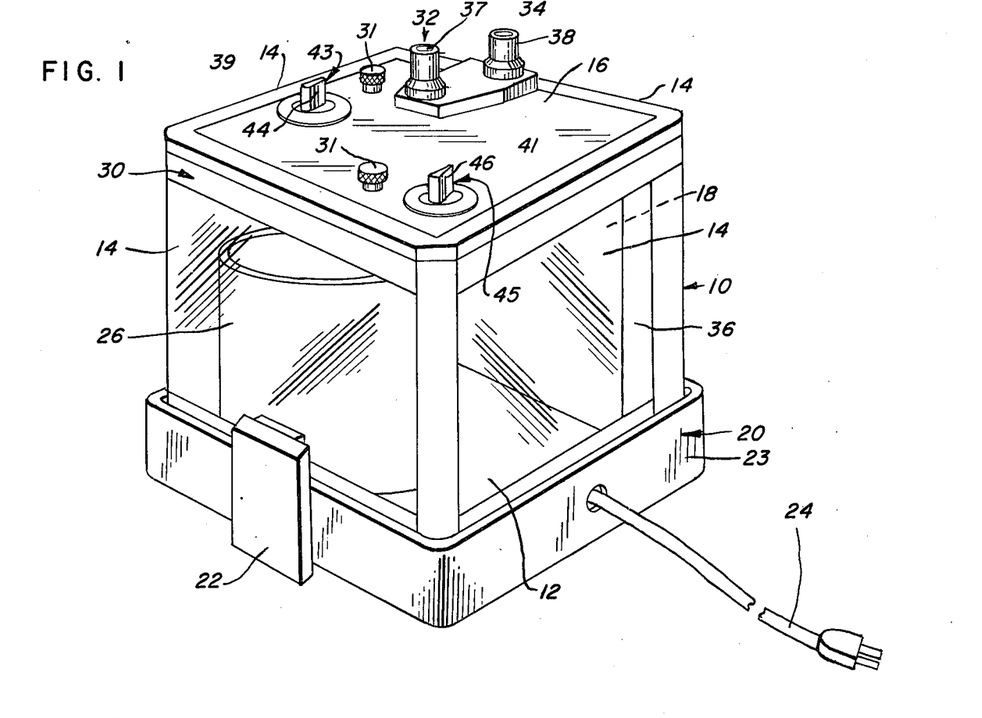
FIG. 1 is a perspective view of the temperature and humidification control device of the present invention.

With particular reference to FIG. 1 of the drawings, the device 10 forming the subject of the present invention is generally illustrated. It will be noted that the device 10 is formed by a bottom wall 12, peripheral side walls 14, and a top wall 16, which together enclose a chamber 18. A removable heater unit 20 is removably secured adjacent the bottom wall 12 by means of lock clips 22 such that in use, the heater 20 is removably secured adjacent the bottom wall 12 such that heat from the heater is permitted to be conductively introduced into the chamber 18 for heating a fluid such as water or the like contained within the chamber 18. In the preferred embodiment, the bottom wall 12 is formed in a conductive material such as a metallic substance, and it has been found that aluminum performs very ably in this connection.

The heater unit 20 is enclosed by a bottom wall (not shown) and side walls 23 thereby to enclose the heating elements (not shown), and the heater unit 20 is of the type which is electrically activated so that the heater is provided with a cord and plug 24 to permit the use of any standard wall socket to provide electrical power to the unit.

As also shown in FIG. 1 of the drawings, the chamber 18 includes a removably positioned heat dispersion cylinder 26 which seats atop the bottom wall 12 and again, is formed of a conductive material, such as preferably aluminum, and functions to disperse the heat emanating from the heater 20 which is conductively brought into the chamber 18 through the bottom wall 12 and conducted outwardly and throughout the interior portion of the chamber due to the coonductivity of the heat dispersion cylinder 26.

Figure 5:
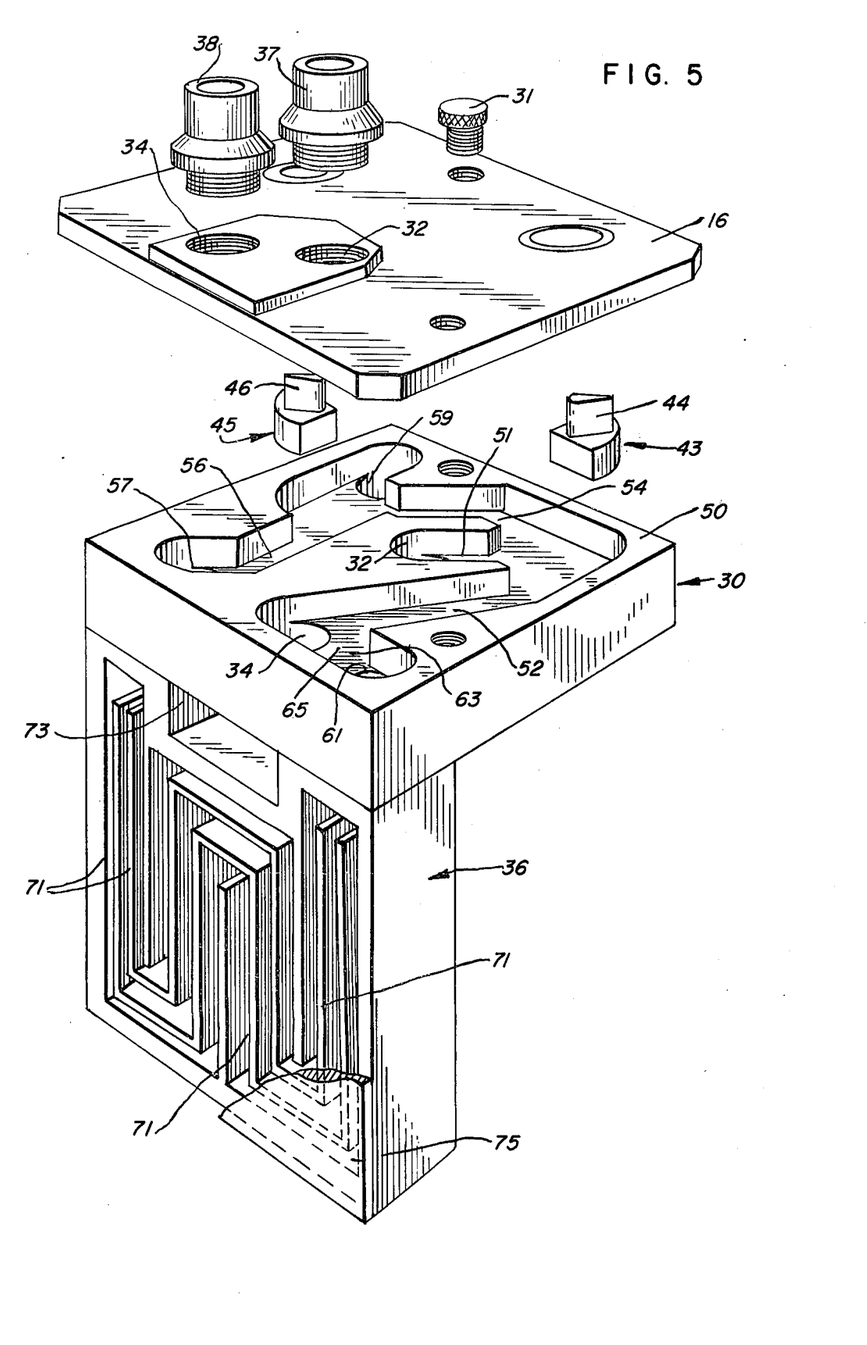
FIG. 5 is a perspective view, partly exploded, showing the relationship between the top wall of the chamber, the gas spider means, and the heat exchanger, all forming a part of the subject device.

As again shown in FIGS. 1 and 5 of the drawings, secured immediately beneath the top wall 16 is a gas spider means, generally referred to by the numeral 30. A pair of threaded lugs 31 positioned through apertures are provided in the top wall 16 and are screwed threadedly secured in apertures provided in the gas spider means 30. Hence, when secured in position, the top wall 16 and gas spider means 30 may be removably positioned within the chamber 18 as a unit. The top wall 16 of the device 10 is shown to be provided with a gas inlet 32 and the gas outlet 34.

Also secured to the bottom portion of the gas spider means 30 is a heat exchanger element 36. It will further be noted that the gas inlet 32 and gas outlet 34 are defined by appropriate nozzles 37 and 38 which may be screw-threaded into position into apertures appropriately provided. As further indicated in FIG. 1, the entire assembly including the top wall 16, gas spider means 30, and heat exchanger element 36 are secured to the device 10 by means of a pair of threaded bolts 39 and 41 respectively. It will therefore be appreciated that the entire assembly including the top wall 16, gas spider means 30, and heat exchanger element 36 may be removed as a unit from the device 10 by merely unfastening the threaded bolts 39 and 41 respectively, and the entire assembly removed. Alternatively, the top wall 16 is removable from the gas spider means 30 by merely unfastening the threaded lugs 31 such that access may then be had to the interior portion of the gas spider means 30 for sterilization, or cleaning purposes or the like.

It will further be observed that the top wall 16 includes appropriate apertures for the positioning of the gas proportioning valves 43 and 45, respectively, which are shown in greater detail in FIG. 5 of the drawings. It will be noted that the outer portions of the values 43 and 45 are each provided with a hand grasp portion 44 and 46, respectively, to permit the operator to grasp and utilize or manipulate the valves 43 and 45.

Figure 6:
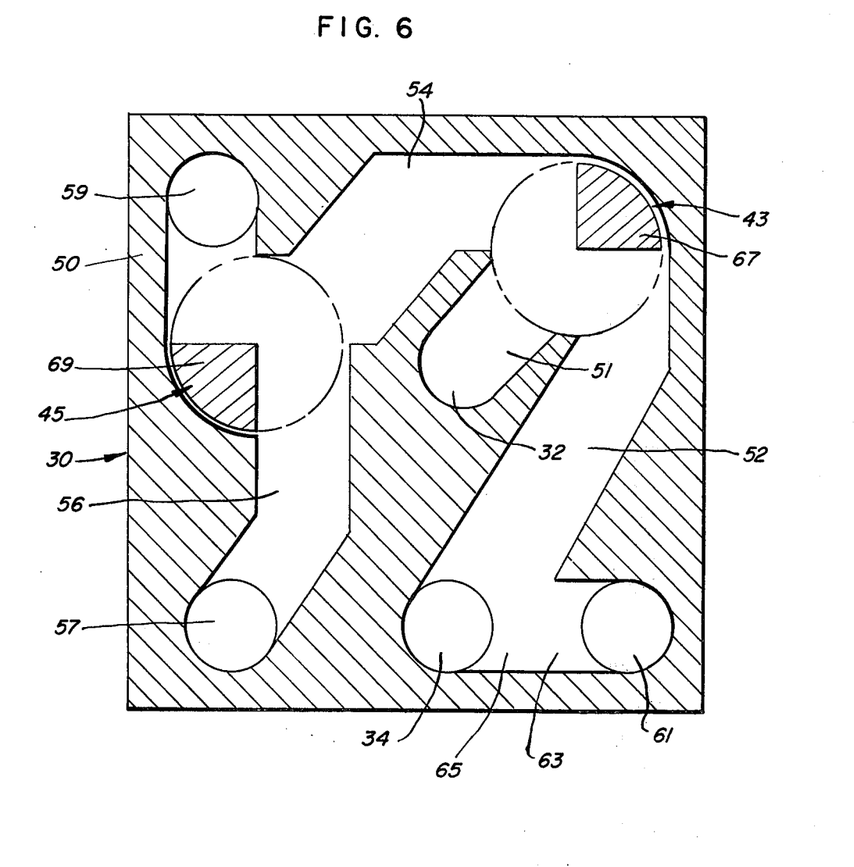
FIG. 6 is a top plan view showing the details of the gas spider means and the gas proportioning valves associated therewith for controlling the proportioning of the gas as the same flows through the gas spider means into the system.

With reference to FIGS. 5 and 6 of the drawings, respectively, the details of the gas spider means 30 are illustrated. It will be observed that the gas spider means 30 is formed by a spider block 50 which, in the ideal embodiment, is formed of a metallic material. The gas passageways are in the block 50 formed by channels which are cut into the block in a manner to be more particularly described hereinafter.

It will be observed that the gas inlet 32 of the device 10 is positioned immediately above a first gas passageway 51 which is formed by a channel cut into the spider block 50. It will be observed from FIG. 6 that the first gas passageway 51 has the first gas proportioning valve 43 interposed in its path. It will be observed that depending upon the positioning of the first gas proportioning valve 43, the first passageway 51 communicates via a second gas passageway 52 with the main gas outlet 34. Additionally, the first gas passageway 51 is in fluid communication with a third gas passageway 54 which, in turn, has the second gas proportioning valve 45 interposed therein. The third gas passageway in turn communicates with a fourth gas passageway 56 which, in turn, leads to the inlet port 57 for the heat exchanger unit 36. It will also be observed that the third gas passageway 54 is in fluid communication with a passageway leading to the chamber inlet port 59 whereby incoming gases may be directed directly into the chamber 18 of the device 10. Once gas has been directed through the fourth gas passageway 56 into the inlet port 57 of the heat exchanger 36, gases will pass through the heat exchanger 36 and exit through the outlet port 61 of the heat exchanger 36. Gases which exit from the outlet port 61 of the heat exchanger 36 will in turn traverse a fifth passageway 63 which is in open communication with a sixth gas passageway 65 immediately surrounding the main gas outlet 34.

In order to fully appreciate the mode of operation of the device 10, the construction of the two gas proportioning valves 43 and 45, respectively, are set forth hereinbelow. Each of the valves 43 and 45 is shown to be formed of basically a 90° angle wedge-shaped member 67 and 69, respectively, which has a height or thickness corresponding to the depth of the gas passageway channels. In addition, it will be observed that the points where the valves 43 and 45 are positioned in the gas passageways, are formed by side walls having a width slightly smaller than, or equal to the circumferential distance between the opposed side ends of the wedge-shaped elements 67 and 69, respectively. It will therefore be appreciated that when each of the wedge-shaped members 67 and 69 are rotated, the same may be positioned to completely occlude a given passageway, or to accurately proportion the amount of gas permitted to flow in any of the two directions exiting from the corresponding gas passageway.

With reference to FIG. 6 of the drawings, it will be observed that upon rotation of the first gas proportioning valve 43, the opening of the first gas passageway 51 into the second gas passageway 52 and third gas passageway 54 may be variably adjusted. In short, in the position as shown in FIG. 6 of the drawings, gas coming in through the main gas inlet 32 is permitted to freely proportion itself into the two gas passageways 52 and 54, respectively. If the first gas proportioning valve 43 is rotated such as to further occlude the opening between the first gas passageway 51 and the third gas passageway 54, a greater portion of the gas will flow through the second gas passageway 52 to the sixth gas passageway 65 surrounding the main gas outlet 34. A relatively smaller portion of the gas will therefore flow through the third gas passageway 54 for further proportioning by the second gas valve 45. Alternatively, if the valve 43 is rotated in the opposing direction, more of the gas will flow through the third gas passageway 54 than will flow through the second gas passageway 52. In effect, the first gas proportioning valve functions as a temperature control valve for the reason that it controls the ratio of gas permitted to flow through the second gas passageway directly to the gas outlet which is cool dry gas and the gas to be heated (whether through the chamber or through the heat exchanger) such that the resulting admixture of gases in the sixth gas passageway 65 immediately adjacent to the main gas outlet 34 will have a gas ratio which can effectively control the gas temperature.

The second gas proportioning valve 45 in effect controls the quantity of gas which is permitted to flow directly into the chamber 18 through the chamber inlet port 59 versus the proportion of gas which is permitted to flow through the fourth gas passageway into the inlet port 57 of the heat exchanger. In effect, therefore, the second gas proportioning valve 45 functions as a humidity control valve since it controls th ratio of hot dry gas to hot wet gas which exits from the system. It will be observed that when the second gas proportioning valve 45 is reciprocated such that the passageway between the third gas passageway 54 and fourth gas passageway 56 is occluded or more occluded, a greater portion of the gas will flow into the chamber inlet port 59 to be heated and humidified in the chamber 18 versus the proportion of gas which will be permitted to flow down the wet gas passageway into the inlet port of heat exchanger 57. Hence, the greater portion of the gas will be heated and humidified such that the quantity of hot wet gas exiting from the system will be greater than the quantity of hot dry gas. The converse may also be controlled by merely rotating the gas proportioning valve 45 to permit more gas to flow through the heat exchanger 36 than will flow through the chamber 18 via the chamber inlet port 59.

Figure 2:
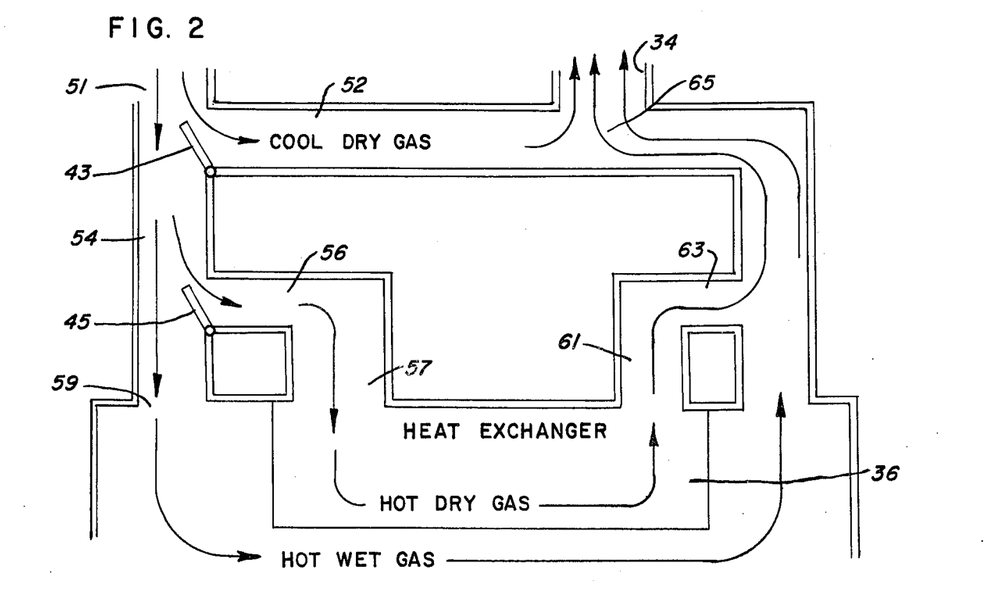
FIG. 2 is a schematic flow diagram showing the manner in which the incoming gas is segregated into three portions for traversing the gas temperature and relative humidity control system of the present invention.
Figure 3:
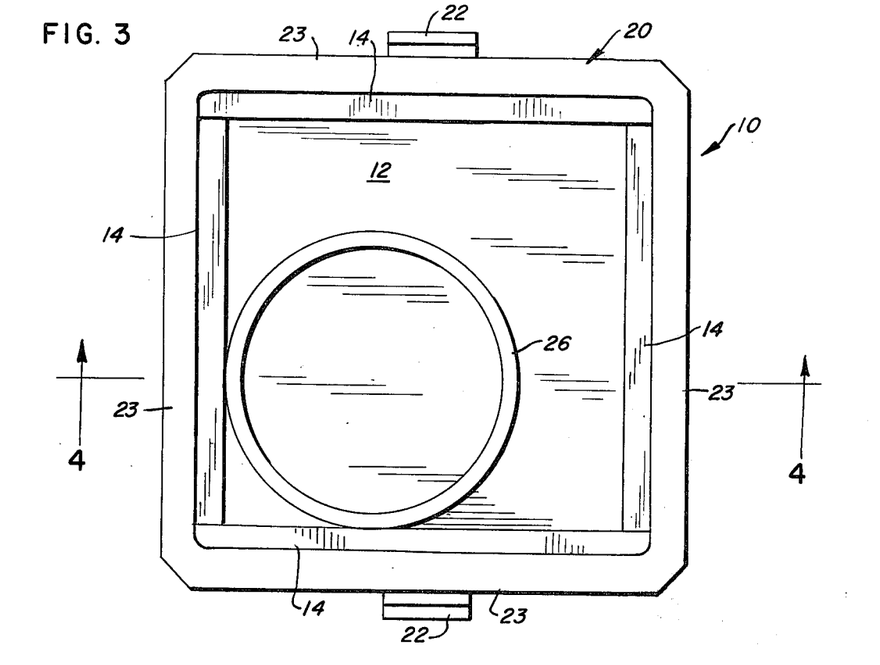
FIG. 3 is a top plan view showing the subject temperature and relative humidity control device with the heat dispersion cylinder positioned therein.
Figure 4:
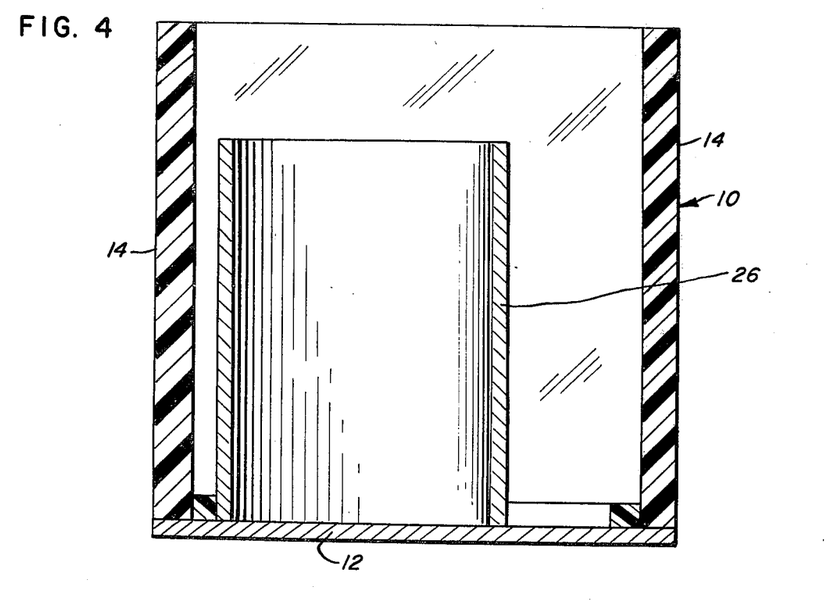
FIG. 4 is a side elevational, cross-sectional view, showing the chamber having the heat dispersion cylinder positioned therein.

With reference to FIG. 2 of the drawings, a schematic illustrating the gas flow paths of the various gases is illustrated. As indicated above, by accurately controlling the positioning of each of the two proportioning valves 43 and 45, respectively, the relative proportion of gas permitted to flow through the system as cool dry gas versus the quantity of gas to flow through the system as hot dry gas, and the quantity to flow through the system as hot wet gas may be regulated such that when the three differently treated gases are admixed in the sixth passageway 65 immediately adjacent to the main outlet port 34 of the system, both temperature and relative humidity of the gas may be accurately controlled. It will further be appreciated that accurate and rapid adjustments may be made by the operator merely by rotating the gas proportioning valves to 43 and 45, respectively, via the hand grasp proportions thereof 44 and 46, respectively.

With respect to the construction of the heat exchanger 36 and the relationship thereof with the gas spider block 50, reference is hereby made to FIG. 5 of the drawings. It will be observed that the heat exchanger 36 is formed in the shape of a rectangular block fixedly secured to the undersurface of the gas spider block 50. The inlet port 57 is in fluid communication with a similar port (not shown) in the heat exchanger unit 36, similarly the outlet port 61 of the gas spider block 50 is in fluid communication with a similar port (not shown), again in the heat exchanger 36. The interior portion of the heat exchanger 36 is shown to include a plurality of fins 71 combining to form a tortuous gas pathway through the heat exchanger 36. The purpose of the tortuous gas pathway through the heat exchanger 36 is to insure that the gas will have a sufficiently long dwell time within the heat exchanger 36 in order to absorb sufficient quantities of heat as the gas traverses the tortuous gas pathway. It will be noted that the construction as set forth above permits the heat exchanger 36 to be immersed within the fluid contained within the chamber 18 during the operation of the device. The heated fluid is permitted to totally surround the heat exchanger 36, and due to the fact that the walls of the heat exchanger 36 are formed of a conductive material, the heat exchanger will absorb heat from the heated fluid in the chamber 18 and transmit the same to the gas as it flows through the exchanger 36.

With respect to the upper portion of the heat exchanger 36, it will be noted that there is an indented U-shaped cutout portion 73 which is positioned immediately below the main gas outlet 34 formed in the gas spider block 50. It will be appreciated that the cutout section 73 is necessary in order to permit gasses which have been heated and humidified in the chamber 18 to pass into the main gas outlet 34 for admixture with the other gases in the sixth gas passageway 65. The construction of the heat exchanger 36 is completed by back wall 75 which is in fluid tight sealing engagement with the main body of the heat exchanger 36 thereby to completely enclose the fins 71 and the tortuous pathway contained within the heat exchanger 36 such that gases dwelling within the heat exchanger 36 can receive only heat and not moisture or vapor.

Having described the constructional features of the invention, the operational features thereof and the advantages obtained thereby are now more clearly ascertainable.

It will be observed that the subject system may be utilized either as a temperature control system alone for gases flowing therethrough, or may be used as a relative humidity control system for the gases, or in the preferred embodiment, this system may be utilized to control both temperature and relative humidity of the exiting gases. In those applications where the device functions to control only relative humidity, the heater unit 20 may be entirely eliminated from the system such that the only two gases which can be proportioned to flow through the device are cool dry gas and cool wet gas. In such an event, only one proportioning gas valve is necessary and functions in a manner to control only the amount of gas being humidified versus the amount of gas flowing through the system unhumidified. Where the heater unit 20 is now added to the system, the system may be utilized to control temperature per se of the exiting gases, or alternatively, may be utilized to control both temperature and relative humidity. Temperature control per se may be achieved by controlling the admixture of cool dry gas with hot wet gas. Hence, one would eliminate the need for the heat exchanger and by controlling the proportion of gas flowing through the system as a cool dry gas versus the amount of gas shunted off into the main portion of the chamber 18 to both heat and humidify the same, the temperature of the resulting gas can be effectively controlled. When utilized as a temperature control system, one arrives at a 100% relative humidity point and the relative humidity cannot actually be adjusted beyond that point. In point of fact, the gas arrives at a high relative humidity at the exiting port but the operator can quickly and precisely control temperature.

The addition of the heat exchanger 36 as of integral part of the gas spider block 50 adds the ability to control both temperature and relative humidity, assuming that one employs a heater unit 20 in conjunction with the system. As indicated previously, the temperature and relative humidity of the exiting gas is controlled by controlling the porportion of cool dry gas, hot dry gas and hot wet gas traversing the system. As indicated previously, the advantage of the present system resides in the fact that the operator need not control the temperature of the heater unit 20 in order to control the temperature of the exiting gas. In addition, the humidity of the gas ceases being a function of the temperature or water content of the fluid in the chamber, but rather, both temperature and relative humidity are easily, rapidly and precisely controlled merely by adjusting the two gas proportioning valves whereby the porportion of cool dry gas to heated gas, with the heated gas being split into hot dry gas and hot wet gas, being ajusted accordingly to a given temperature and relative humidity control setting.

Another variation of the present system contemplates that the incoming gas flowing into the system through the gas inlet may be initially split by a first gas proportioning valve into cool dry gas and a gas to be heated. The gas to be heated could then, in turn, be shunted completely through the heat exchanger such as to create a quantity of hot dry gas, with none of the gas at that point being sent through the humidifier. The gas exiting from the humidifier could then be shunted through the gas spider block to a gas passageway which would contain another proportioning valve such that some of the gas would at that point be shunted off into the main chamber where heated water is contained. This would permit a more rapid heating of the gas since all of the gas to be heated would be first exposed to the heat exchanger prior to shunting any of the gas in the chamber to be humidified. It will be appreciated that by modifying the system in this manner, the gas could be heated more quickly permitting even more efficient and precise controlling by the operator to control both temperature and relative humidity. It will also be appreciated that to adapt the system in this manner would only involve rechannelling the gas as the same traverses the gas spider block 50 and to provide appropriate passageways with inlet ports and outlet ports such that all of the gas to be heated is first sent through the heat exchanger prior to proportioning the gas for subsequent passage into the main chamber for humidification purposes.

With regard to the heater unit employed in the subject system, it will be appreciated that the need for an adjustable thermostat is completely eliminated. In fact, one could employ a single temperature heater such that the only thermostat is the one incident to the heater and that involving only a single setting type thermostat so that the heater would only heat one temperature, that is, at approximately 200° F. The fact is that the heater may now be located externally to the system and may be completely removed when cleaning and sterilizing the remaining structure of the system.

As to the humidification chamber, it is contemplated that the chamber would be formed of the bottom wall 12 formed of a heat conductive material such as a metal palette preferably aluminum, which easily and efficiently conducts heat. The peripheral side walls 14 can be formed of any plastic material which is heat and moisture resistant there being a seating engagement between the bottom wall 12 and the peripheral side walls 14. The top wall 16 may similarly be formed of a plastic material which has a high tolerance for heat and moisture such that the overall cost of manufacturing the chamber would be held to a minimum.

The gas spider block 50 is contemplated to be formed of a plastic material and may be actually manufactured by a molding process. Alternatively, the block may be formed of a metallic material and the gas passageways simply cut into the block as a method of manufacture. The important aspect of the formation of the gas spider block 50 relates to the tolerances which exist between the gas proportioning valves 43 and 45, respectively, and the gas passageways which are tended to be occluded by the subject valves 43 and 45. The tolerances must be held reasonably close so that once the valves 43 and 45 respectively are in position, the corresponding passageways may be completely occluded, or partially occluded as the case may be.

The cylindrical element which functions as a heat dispersion means, designated by the numeral 26, is contemplated to be formed of a conductive metallic material. Since the cylindrical element 26 seats atop the bottom wall 12, the heat which is picked up from the heater unit 20 can easily be conducted by the element 26 throughout the interior portion of the chamber. Once again, the presence of the heat dispersion cylinder 26 merely insures that the water contained within the chamber 18 will be more uniformly heated during the use of the subject device 10, and therefore, it will be appreciated that the element 26 may be completely eliminated. As indicated previously, the heat exchanger 36 is fixedly secured to the gas spider block 50 and the only requirement for the heat exchanger 36 is that it provides sufficiently long dwell time of the gas as the same traverses therethrough. This is accomplished by providing a tortuous gas pathway provided with a plurality of fins 71 such that the gas dwells a sufficiently long time within the heat exchanger 36 to absorb the heat which is picked up by the heat exchanger 36 from the heated water in the chamber 18.

As to the gas proportioning valves, it has been found that if the same are constructed in the form of a 90° wedge-shaped core, the functional result desired within the scope of the present invention may be achieved. It will be appreciated that by rotating the subject 90° wedge-shaped elements, a given passageway may be completely occluded or only partially occluded as desired by the operator. This permits the operator to precisely and accurately control the amount of gas to be shunted down any given passageway within the gas spider block 50 in order to achieve the desired admixture of cool dry gas to hot wet gas to hot dry gas.

One of the advantages obtained by the device 10 of the present invention is that the temperature and relative humidity of the gas can be so controlled that when the gas exits from the humidifier and passes down the tubing system to the patient — supported inhalation means such as a face mask, there is virtually no condensation of moisture within the tubing system. The present system permits sufficient control of temperature and relative humidity such that as the gas passes down the tubing system to the patient, and the temperature is reduced during the course of travel down the system, relative humidity will be increased due to the inverse relationship between the temperature and humidity. In other words, as the temperature of the gas falls during the course of travel down the tubing system, the relative humidity of the gas mixture will increase. It can be shown that where the relative humidity of the gas mixture does increase during the path travel, condensation or moisture fallout from the gas passing down the tubing system is virtually eliminated.

In the preferred embodiment as described herein, the same is scaled with fairly large relative dimensions which thereby reduce or minimize the resistance of the overall system. That is, the resistance to gas flow is reduced to an absolute minimum factor. However, the present system can be adapted to be reduced in scale or size decreasing the dimensions thereof having a resulting increase in resistance in the system to gas flow. Where this is desired, it will be appreciated that where the system is reduced in dimensions and proportions to a sufficiently small size, it would be necessary to employ gas under pressure in order to effectively utilize the system, Hence, where the system is scaled down by decreasing the dimensions of the various gas passageways and the like, the system can be made applicable to the use of gas under pressure in those types of therapy where compressed gas is presently used. Alternatively, by leaving the system in the present form, with relatively large dimension, the system is easily adapted to the use of a venturi entrainment system. It should be pointed out, however, that the present system in its present form can be used with gas under pressure, such as with ventilators That is, the system as presently contemplated having relatively large dimensions with minimal resistance can be employed whether the system is intended to be used in connection with a source of gas under pressure or where little to no such gas pressure is employed. The fact of the matter is, that when the system is scaled down by decreasing the dimensions, it is possible to employ the same system conceptually to a heated humidifier control system useful in connection with a system where gas is provided under pressure where such applications are now used.

It is also contemplated to be within the scope of the present invention to provide a passageway leading directly from the gas inlet 32 directly into the chamber 18. The opening or passageway would be of relatively small dimensions, but would nevertheless insure that at all times that device is operational, a certain quantity of gas will always pass into the chamber and be humidified. This will thereby serve as a safety feature to insure that a certain amount of gas will always be humidified for delivery to the patient.

It will be appreciated that by virtue of the present invention, an effective system has been provided which can control the temperature and relative humidity of a gas to be introduced to a patient's breathing system especially adapted for respiratory therapy. In effect, both temperature and relative humidity of the resulting gas exiting from the system may be controlled without the need to adjust either the heater thermostat involved with the heater humidifier, or the amount of water residing within the humidification chamber. In effect, the system of the present invention employs a gas spider means which includes two gas proportioning valves such that the gas traversing through the gas spider means is proportioned to form a cool dry gas, a hot wet gas, and a hot dry gas, whereupon admixture of the three types of gases, both the temperature and relative humidity of the exiting gas may be efficiently and accurately controlled. In addition, the subject system permits rapid system response to the operator's exchange of parameters such that the operator may quickly change the temperature or relative humidity or both of the exiting gases, the system responding in a very brief period of time to changes in the controls.

While there has been described what is at present considered to be the preferred embodiments of the invention, it will be understood that various modifications may be made therein and it is intended to cover in the impended claims all such modifications as fall within the true spirit and scope of the invention.

What is claimed is:

1. A device for controlling the relative humidity of a gas utilized in connection with a lift support system comprising, in combination, a chamber bounded by a bottom wall, peripheral side walls, and a top wall, and adapted to receive and hold a quantity of fluid for humidifying a gas therein, said chamber provided with a gas inlet and a gas outlet, gas spider means associated with said gas inlet, said gas spider means providing gas passageways for segregating portions of said gas provided to said system through said gas inlet, gas proportioning valve means positioned in association with said gas spider means and in line with said gas inlet thereby to permit the independent variable proportioning of gas to at least two down line gas passageways, at least a first passageway traversing said gas spider means and terminating at said gas outlet, and at least a second gas passageway traversing said gas spider means and in fluid communication with said chamber, said gas outlet being in fluid communication with said chamber and with said first passageway in said gas spider means, whereby gas introduced into said system through said gas inlet may be variably adjusted to direct a portion of said gas through said gas spider means to said gas outlet and another portion of said gas directed to a second passageway for introduction into said chamber to humidify the same and exiting said humidified gas into a passageway to mix with said first gas portion thereby forming a gas mixture having a controlled relative humidity.

2. A device for independently controlling the temperature of a gas utilized in connection with a life support system comprising, in combination, a chamber bounded by a bottom wall, peripheral side walls, and a top wall, said chamber adapted to contain a quantity of a fluid for humidifying gases, heat means associated with said chamber for providing heat to the internal portion of said chamber, at least one of said walls of said chamber provided with a gas inlet and a gas outlet, gas spider means associated with said gas inlet, said gas spider means providing gas passageways for segregating portions of said gas provided to said system through said gas inlet, gas proportioning valve means positioned in association with said gas spider means and in line with said gas inlet thereby to permit the independent variable proportioning of gas to at least the two down line gas passageways, at least a first gas passageway traversing said gas spider means and terminating at said gas outlet, and at least a second gas passageway traversing said gas spider means and in fluid communication with said chamber, said gas outlet being in fluid communication with said chamber and with said first passageway in said gas spider means whereby gas introduced into said system through said inlet may be variably adjusted to direct a portion of said gas through said gas spider means to said gas outlet and another portion of said gas directed to another passageway for introduction into said chamber thereby to heat and humidify the same, and exiting said gas into a passageway to form a gas mixture with said first gas portion thereby forming a gas mixture having a temperature which may be variably adjusted by the operator to a preset value.

3. The temperature control device as set forth in claim 2 above, wherein said heat means associated with said chamber is provided adjacent the bottom wall thereof.

4. The temperature control device as set forth in claim 3 above, which further includes heat dispersion means associated with said chamber uniformly throughout.

5. The temperature control device as set forth in claim 4 above, wherein said heat dispersion means comprises a vertically elongate heat conducted element positioned on the bottom wall of said chamber such that heat emanating from the bottom wall thereof is caused to be uniformly distributed and dispersed throughout the said chamber.

6. The temperature device as set forth in claim 2 above, wherein said heat means comprises an externally mounted heater mounted adjacent said bottom wall and adapted to radiate heat to said bottom wall such that heat emanates from said bottom wall and is permitted to warm the internal portions of said chamber.

7. The temperature control device as set forth in claim 2 above, wherein said gas spider means comprises a channelled element including a first passageway positioned immediately below and adjacent said gas inlet, said first passageway being in communication with a second passageway which in turn is in communication with said gas outlet, a third passageway in open communication with said first passageway which, in turn, is in open communication with said chamber, and at least a first gas proportioning valve means interposed between said first passageway and said second and third passageways such that the manipulation of said gas proportioning valve means controls the gas flow through said gas inlet and said first passageway to said second and third gas passageways, such that the manipulation of said gas proportioning valve means controls the ratio of gas and the gas flow through either of said second and third gas passageways respectively.

8. The temperature control device as set forth in claim 7 above, wherein said gas spider means is provided with a fourth passageway in open communication with said third gas passageway, and which further includes heat exchanger means associated with said gas spider means, said heat exchanger means having a gas inlet in open communication with said fourth passageway, said gas spider means further including a fifth passageway in open communication with a gas outlet from said heat exchanger, and further including at least a second gas proportioning valve means interposed between said third and fourth gas passageways and said gas spider means thereby to proportion and control gas flow through either of said third and fourth passageway such that upon manipulation of said second gas proportioning valve means, the gas flow through said third and fourth passageways and through said heat exchanger means may be controlled thereby to proportion and control the amount of gas flowing into said chamber directly and through said heat exchanger respectively, thereby to effect control of both temperature and relative humidity of the exiting gas.

9. The temperature and relative humidity control device as set forth in claim 8 above, wherein said gas spider means further includes a sixth passageway in open communication with said chamber and with said fifth passageway and further in open communication with said gas outlet of said chamber such that all gases exiting from said chamber and from said device are intermixed in said sixth gas passageway at the point of exiting from said device through said gas outlet.

10. The temperature and relative humidity control device as set forth in claim 8 above, wherein said heat exchanger means comprises a vertically elongate gas chamber provided with a tortuous gas passageway therein, and said vertically elongate gas chamber being adapted to sit within said chamber but in fluid tight relationship with respect to liquids contained within said chamber such that the interior portion of said elongate gas chamber is fluid-tight and impervious to any liquids within said chamber such that any gas passing through said heat exchanger means is retained in dry condition.

11. The temperature and relative humidity control device as set forth in claim 10 above, wherein said heat exchanger means is fixedly secured to said gas spider means and wherein the interior portion of said gas chamber is in fluid communication with said fourth and fifth passageways in said gas spider means and wherein the heat emanating from said heat means associated with said chamber functions to heat the interior portion of said heat exchanger means thereby to heat any gases traversing the tortuous passageway contained therein whereby gas is flowing through said heat exchanger means may only be heated.

12. The temperature device as set forth in claim 2 above, wherein said gas proportioning valve means comprises an elongate member having an occlusion member, said occlusion member constructed and designed for interposition between at least two passageways in said gas spider means thereby to permit the variable occlusion of each of the said two gas passageways.

13. The temperature device as set forth in claim 12 above, wherein said occlusion member is constructed in the form of a right angle wedge element and is rotatably positioned in interposed relationship between at least two passageways such that upon rotation of said wedge-shaped element, each of the two passageways may be variably occluded.

14. The temperature and relative humidity control device as set forth in claim 9 above, wherein said device is provided with two gas proportioning valve means, each of said gas proportioning valve means comprising an elongate member including a 90° angled wedge-shaped occlusion member, said occlusion member of said first gas proportioning valve being rotatably interposed between said second and third passageways in said gas spider means, and said occlusion member of said second gas proportioning valve being rotatably interposed between said third and fourth passageways, such that upon the rotational movement of each of said two gas proportioning valves, the operator may variably occlude each of said second and third gas passageways with respect to one another and may similarly variably occlude either of said third and fourth gas passageways with respect to one another such that gas flowing through said gas inlet of said device may be proportioned to flow partially through said second gas passageway and to said gas outlet, and partially through said third gas passageway into said chamber, and similarly, said second gas proportioning valve is rotatably interposed between said third and fourth passageways such that upon rotational movement of said second gas proportioning valve, gas may be proportioned to flow partially through said third passageway into said chamber and partially through said fourth passageway into said heat exchanger, the gas flowing through said third gas passageway and into said chamber establishing a flow path directly into said sixth gas passageway and said gas flowing through said fourth gas passageway establishing a gas flow path through said heat exchanger to said fifth passageway, all of the gases flowing through said device intermixing in said sixth gas passageway immediately prior to exiting through said gas outlet of said device for down line delivery whereby the heat and relative humidity of said exiting gas is fully controllable.

15. The temperature and relative humidity control device as set forth in claim 14 above, wherein gas flowing through said second passageway of said spider means remains in a cool dry condition, while gas flowing through said third gas passageway and through said chamber into said sixth gas passageway is in a hot wet condition, and gas flowing through said fourth passageway through said heat exchanger, said fifth passageway and into said sixth passageway is in a hot dry condition, whereby upon the intermixing of said cool dry gas, hot wet gas, and hot dry gas, the temperature and relative humidity of the resulting gas mixture may be effectively and quickly controlled by the rotational adjustment of said two gas proportioning valves which in turn controls the relative amount of cool dry gas, hot wet gas, and hot dry gas which is permitted to intermix in the sixth passageway of said gas spider means.

16. The temperature control device as set forth in claim 2 above, wherein said top wall is removeably positioned atop said gas spider means such that upon removal of said top wall, access may be had to said gas spider means.

17. The temperature control device as set forth in claim 16 above, wherein said top wall may be fixedly secured to said gas spider means such that upon removal of said top wall, said top wall and said gas spider means may be removed from said chamber as a unit.

18. The temperature control device as set forth in claim 17 above, wherein said heat exchanger means is fixedly secured to said gas spider means, whereby said heat exchanger means, gas spider means, and top wall may be fixedly secured one to the other and removed from said device as a unit.

19. A device for independently controlling the temperature and relative humidity of a gas utilized in connection with a life support system comprising, in combination,
  a chamber bounded by a bottom wall, peripheral side walls, and a top wall, said chamber adapted to contain a quantity of a fluid for humidifying gases, heat means associated with said chamber for providing heat to the internal portion of said chamber, at least one of said walls of said chamber provided with a gas inlet and a gas outlet, gas spider means associated with said gas inlet, said gas spider means providing gas passageways for segregating portions of said gas provided to said system through said gas inlet, gas proportioning valve means positioned in association with said gas spider means and in line with said gas inlet thereby to permit the independent variable proportioning of gas in said system, a first gas passageway traversing said gas spider means and terminating at said gas outlet, a second gas passageway traversing said gas spider means and in fluid communication with said chamber, a third gas passageway in open communication with said first passageway.

a fourth gas passageway in open communication with said third gas passageway, and which further includes heat exchanger means associated with said gas spider means, said heat exchanger means having a gas inlet in open communication with said fourth passageway, said gas spider means further including a fifth passageway in open communication with a gas outlet from said heat exchanger, a first gas proportioning valve interposed between said first passageway and said second and third passageways such that the manipulation of said gas proportioning valve means controls the gas flow through said gas inlet and said first passageway to said second and third gas passageways, such that the manipulation of said gas proportioning valve means controls the ratio of gas and the gas flow through either of said second and third gas passageways respectively, a second gas proportioning valve means interposed between said third and fourth gas passageways and said gas spider means thereby to proportion and control gas flow through either of said third and fourth passageway such that upon manipulation of said second gas proportioning valve means, the gas flow through said third and fourth passageways and through said heat exchanger means may be controlled thereby to proportion and control the amount of gas flowing into said chamber directly and through said heat exchanger respectively, thereby to effect control of both temperature and relative humidity of the exiting gas, said gas outlet being in fluid communication with said chamber and with said first passageway in said gas spider means whereby gas introduced into said system through said inlet may be variably adjusted to direct a portion of said gas through said gas spider means to said gas outlet and another portion of said gas directed to another passageway for introduction into said chamber thereby to heat and humidify the same, and exiting said gas into a passageway to form a gas mixture with said first gas portion thereby forming a gas mixture having a temperature and relative humidity which may be variably adjusted by the operator to any desired combination.

* * * * *